(12) United States Patent
Barnhart (10) Patent No.: US 6,361,541 B1
(45) Date of Patent: Mar. 26, 2002

(54) SURGICAL INSTRUMENT FOR EXTRACTING TISSUE INGROWTH FROM A PERMEABLE MEMBER OF AN IMPLANTED CATHETER

(75) Inventor: William H. Barnhart, Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/118,586

(22) Filed: Jul. 17, 1998

(51) Int. Cl.[7] .................................................. A61F 11/00
(52) U.S. Cl. ............................................................ 606/108
(58) Field of Search ................................. 606/104, 108, 606/107, 110, 190; 433/159; 604/106

(56) References Cited

U.S. PATENT DOCUMENTS

| 673,598 | A | * | 5/1901 | Dolge | 606/108 |
|---|---|---|---|---|---|
| 3,653,388 | A | | 4/1972 | Tenckhoff | 128/347 |
| 4,266,999 | A | | 5/1981 | Baier | 156/227 |
| 4,405,313 | A | | 9/1983 | Sisley et al. | 604/43 |
| 4,484,911 | A | | 11/1984 | Berlin et al. | 604/174 |
| 4,574,800 | A | | 3/1986 | Peers-Trevarton | 128/303 |
| 4,585,437 | A | * | 4/1986 | Simms | 604/106 |
| 4,608,982 | A | * | 9/1986 | Pollard | 606/190 |
| 4,655,218 | A | * | 4/1987 | Kulik et al. | 128/132 |
| 4,676,782 | A | | 6/1987 | Yamamoto et al. | 604/175 |
| 4,889,112 | A | * | 12/1989 | Schachner et al. | 606/108 |
| 5,292,324 | A | * | 3/1994 | McDonald | 606/107 |
| 5,580,344 | A | | 12/1996 | Hasson | 600/219 |
| 5,651,767 | A | | 7/1997 | Schulman et al. | 604/8 |
| 5,693,069 | A | * | 12/1997 | Shallman | 606/110 |
| 5,697,936 | A | | 12/1997 | Shipko et al. | 606/108 |
| 5,725,532 | A | * | 3/1998 | Shoemaker | 606/104 |
| 5,772,670 | A | * | 6/1998 | Brosa | 606/108 |
| 5,910,155 | A | * | 6/1999 | Ratcliff et al. | 606/213 |

FOREIGN PATENT DOCUMENTS

EP 0815893 A1 10/1996

* cited by examiner

Primary Examiner—Cary E. O'Connor
(74) Attorney, Agent, or Firm—Woodard, Emhardt, Naughton, Moriarty & McNett (57) ABSTRACT

A surgical instrument for extracting tissue ingrowth from a permeable member of a catheter implanted in a patient is disclosed. The surgical instrument includes a first extracting component and a second extracting component pivotally coupled to the first extracting component. Both extracting components include a wedge having a blunted leading edge sized and shaped to be lodged adjacent an adhesion interface between the permeable member and tissue of a patient when the extracting components are pivoted to a closed position. The extracting components can then be pivoted to an open position to forcibly pull the tissue ingrowth out of the permeable member. Each wedge further has a concave surface sized and shaped such that, after the complete extraction of the tissue ingrowth from the permeable member, the wedges can clench the permeable member when the first extracting component and the second extracting component are pivoted to a closed position.

8 Claims, 14 Drawing Sheets

SURGICAL INSTRUMENT FOR EXTRACTING TISSUE INGROWTH FROM A PERMEABLE MEMBER OF AN IMPLANTED CATHETER

BACKGROUND OF THE INVENTION

1. Field of the Invention

The present invention relates to the field of surgical instrumentation. More particularly, the present invention relates to surgical instruments which are used to remove an implanted catheter from a patient.

2. Background

Figure 1:
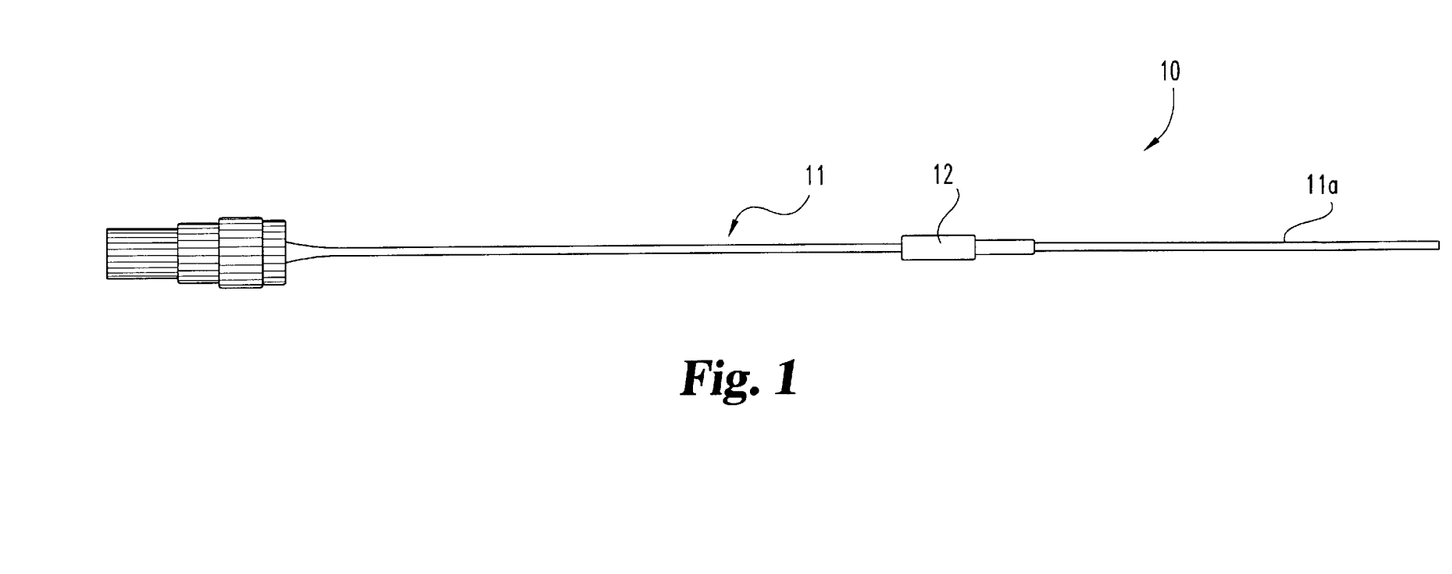
FIG. 1 is a longitudinal view of a Cook TPN™ (Total Parenteral Nutrition) single lumen catheter.
Figure 2:
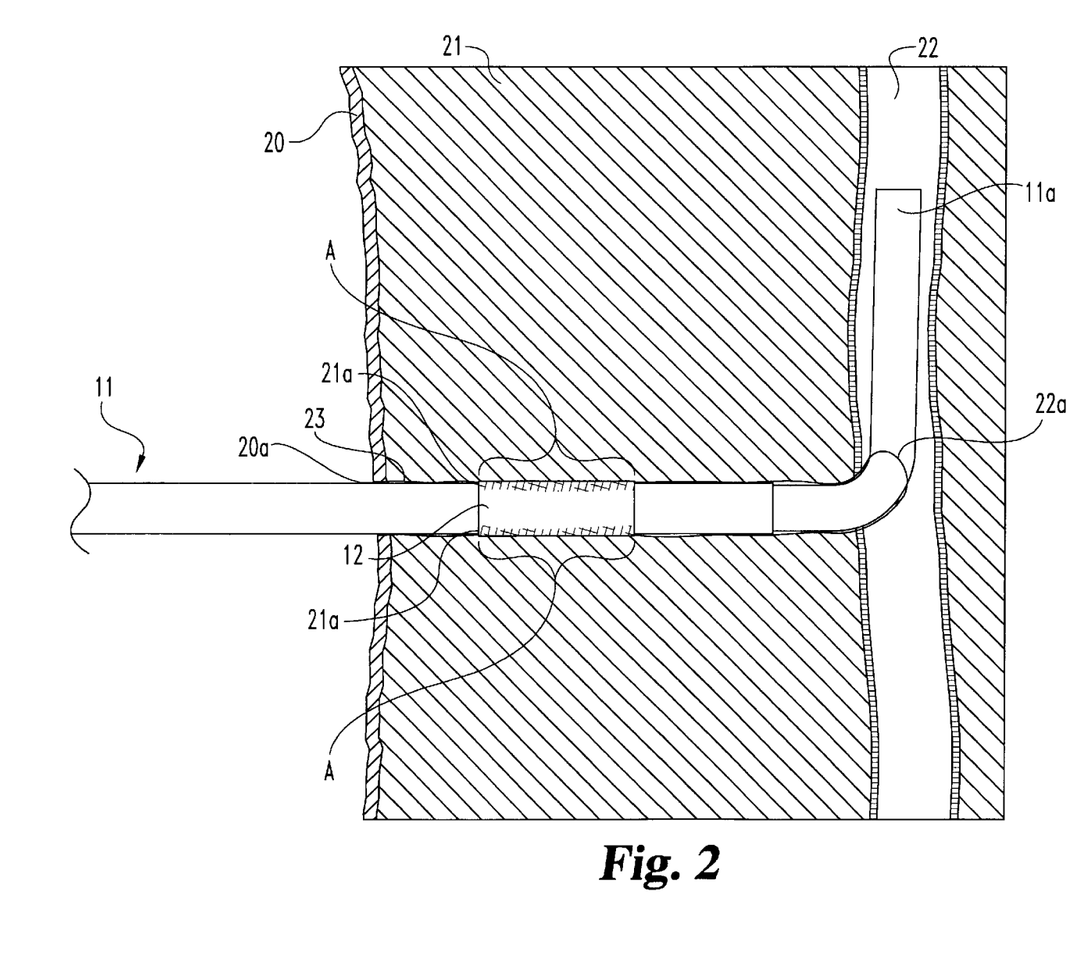
FIG. 2 is a view of a catheter tube and a Dacron™ cuff of the catheter of FIG. 1 implanted in a fragmented, cross-sectional view of a patient.
Figure 3:
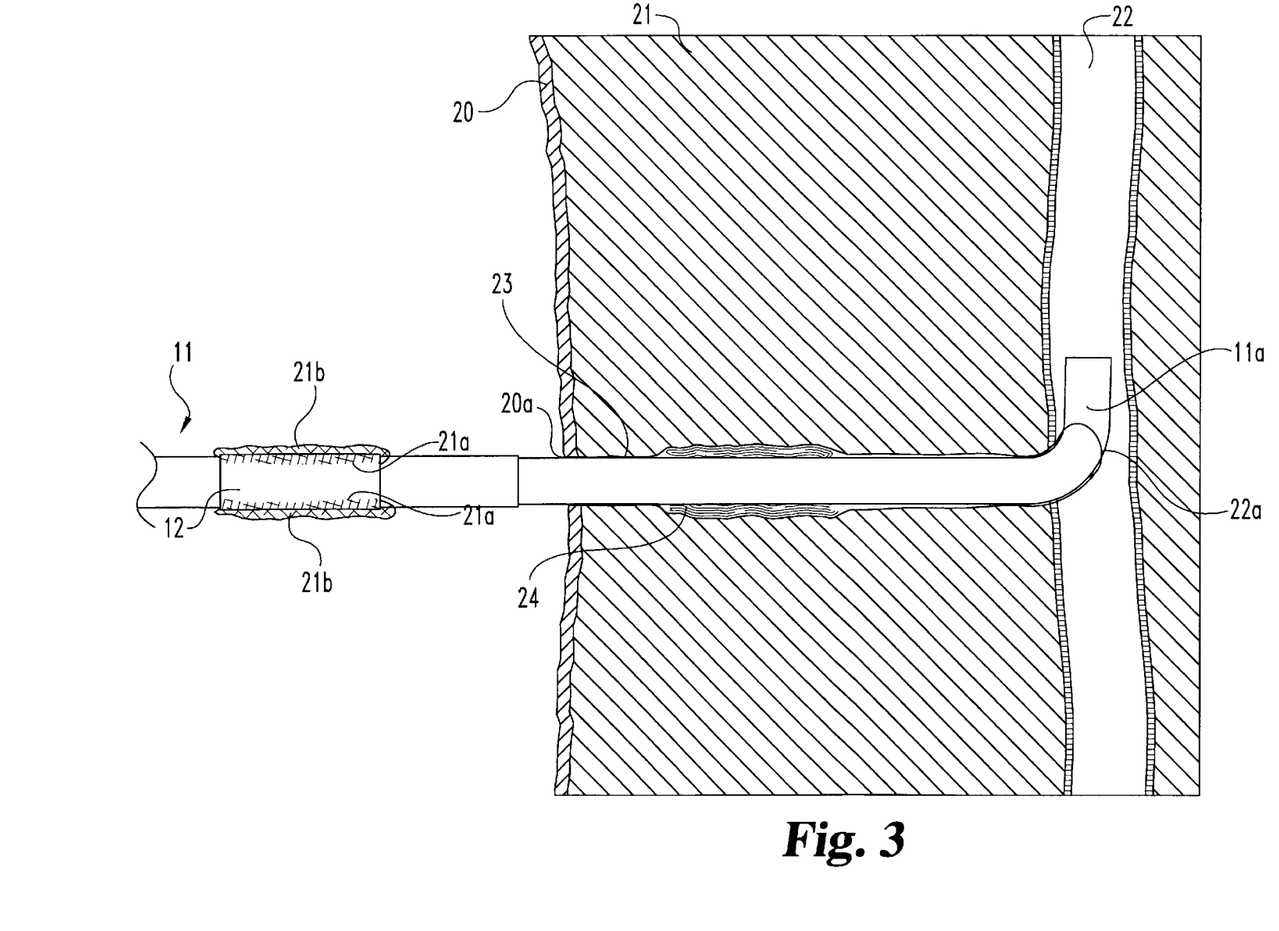
FIG. 3 is a view of the catheter tube and the cuff of the implanted catheter of FIG. 2 dissected from the patient of FIG. 2.

Catheters are surgically implanted in a patient when it is necessary to provide medications, blood products, liquid food, etc. to the patient for a significant amount of time. It is essential is such cases that the implanted catheter is anchored within the patient. One approach to anchoring the implanted catheter is the placement of a permeable member of the implanted catheter inside the patient to promote tissue ingrowth within the permeable member. Typically, the permeable member is either a catheter tube or a cuff affixed around the catheter tube as described in U.S. Pat. Nos. 4,266,999, and 4,405,313, hereby incorporated by reference. A commercial example of a cuff is a Dacron® cuff 12 of a Cook TPN™ (Total Parenteral Nutrition) single lumen catheter 10 as shown in FIG. 1. Referring to FIGS. 1 and 2, an illustrative implantation of catheter 10 involves surgically creating a subcutaneous tunnel 23 through a skin 20 and a tissue 21 of the patient to a blood vessel 22 of the patient, inserting a distal end 11a of a catheter tube 11 of catheter 10 through subcutaneous tunnel 23 into blood vessel 22, and positioning cuff 12 midway between a skin entry point 20a and a blood vessel entry point 22a. Subsequently, tissue adhesion occurs along an interface A of cuff 12 and tissue 21 to promote ingrowth of a portion 21a of tissue 21 within cuff 12 as shown in FIG. 2. As a result, portion 21a of tissue 21 anchors catheter tube 11 within the patient. Upon completion of the treatment, catheter tube 11 must be removed from the patient. Presently, a cutting instrument, e.g. a scalpel, is utilized to dissect cuff 12 away from tissue 21. Referring to FIG. 3, the drawbacks associated with the utilization of a cutting instrument are the concurrent dissection of portion 21a and a portion 21b of tissue 21 away from tissue 21, the difficulty in minimizing the amount of portion 21b of tissue 21 that is dissected with cuff 12, and the promotion of a substantial amount of bleeding at 24 throughout subcutaneous tunnel 23.

SUMMARY OF THE INVENTION

The present invention provides a new and unique surgical instrument for removing an implanted catheter which operates to extract tissue ingrowth from a permeable member of an implanted catheter. The surgical instrument is easy and convenient to use, and overcomes the aforementioned drawbacks associated with the utilization of a scalpel to dissect tissue adhering to the permeable member of the implanted catheter.

As shown in the following description of the preferred embodiments, a surgical instrument is operable to extract a tissue ingrowth out of a permeable member of a catheter implanted in a patient by forcibly pulling the tissue ingrowth out the permeable member. The surgical instrument comprises a first extracting component including a first wedge having a blunted leading edge, and a second extracting component including a second wedge having a blunted leading edge. The extracting components are pivotally coupled to move the wedges to a closed position or to an open position. The blunted leading edges of the wedges are sized and shaped to be lodged adjacent an adhesion interface of the permeable member and the tissue of the patient when the wedges are in the closed position. As a result, the wedges can be pivotally moved to the open position to forcibly pull the tissue ingrowth out of the permeable member.

It is an object of the present invention to provide a surgical instrument for removing a catheter implanted within a patient which is operable to forcibly pull tissue ingrowth out of a permeable member of the catheter without any deliberate dissection of the permeable member away from the tissue of the patient.

It is another object of the present invention to provide a surgical instrument for removing a catheter implanted within a subcutaneous tunnel of a patient which minimizes the amount of blood induced throughout the subcutaneous tunnel as the catheter is being removed.

These and other objects and advantages of the present invention will become more apparent from a review of the following description of the preferred embodiments.

DESCRIPTION OF THE PREFERRED EMBODIMENTS

For the purposes of promoting an understanding of the principles of the present invention, reference will now be made to the preferred embodiments illustrated in the drawings and specific language will be used to describe the same. It will nevertheless be understood that no limitation of the scope of the present invention is thereby intended, such alterations and further modifications in the illustrated embodiments and such further applications of the principles of the present invention as illustrated therein being contemplated as would normally occur to one skilled in the art to which the present invention relates.

Figure 4A:
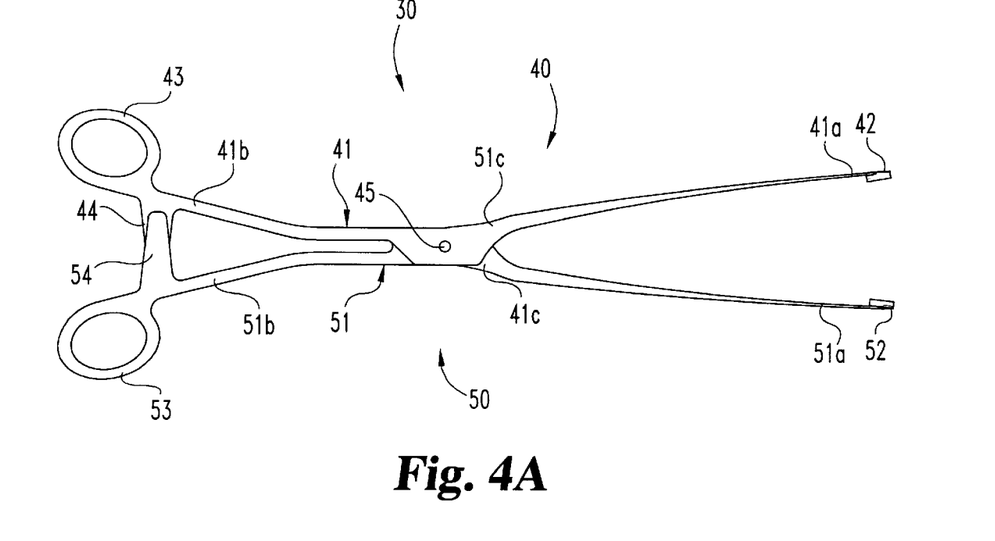
FIGS. 4A–4B are longitudinal views of a first preferred embodiment of a surgical instrument for extracting tissue ingrowth from the cuff of the implanted catheter of FIG. 2.
Figure 4B:
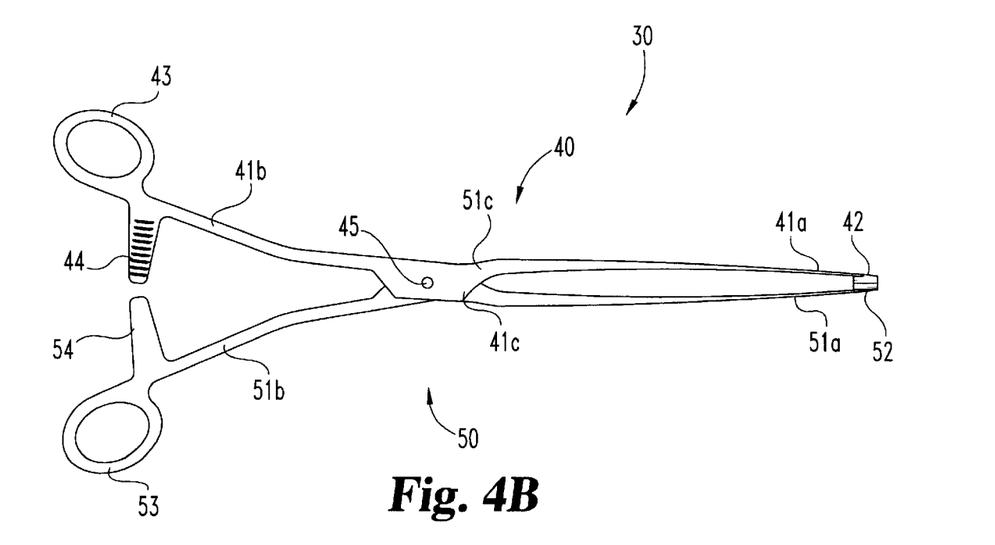

FIGS. 4A and 4B are longitudinal views of a surgical instrument 30 according to a first preferred embodiment of the present invention. Referring to FIGS. 4A and 4B, surgical instrument 30 comprises a first extracting component 40, and a second extracting component 50. First extracting component 40 includes an arm 41, a wedge 42 integrated to a distal end 41a of arm 41, a finger hole 43 integrated to a proximal end 41b of arm 41, a saw tooth 44 integrated to proximal end 41b of arm 41, and a pivot pin 45 integrated to a middle section 41c of arm 41. Second extracting component 50 includes an arm 51, a wedge 52 integrated to a distal end 51a of arm 51, a finger hole 53 integrated to a proximal end 51b of arm 51, and a saw tooth 54 integrated to proximal end 51b of arm 51. A middle section 51c of arm 51 is pivotally coupled to pivot pin 45 to thereby allow a user of surgical instrument 30 to move wedge 42 and wedge 52 to an open position and a closed position via finger hole 43 and finger hole 53. An open position of wedge 42 and wedge 52 is with an engagement of saw tooth 44 and saw tooth 54 to some extent as shown, for example, in FIG. 4A. A closed position of wedge 42 and wedge 52 is with a disengagement of saw tooth 44 and saw tooth 54 to some extent as shown, for example, in FIG. 4B. Wedge 42 and wedge 52 constitute a radially expandable wedge assembly when in the closed position.

Figure 5A:
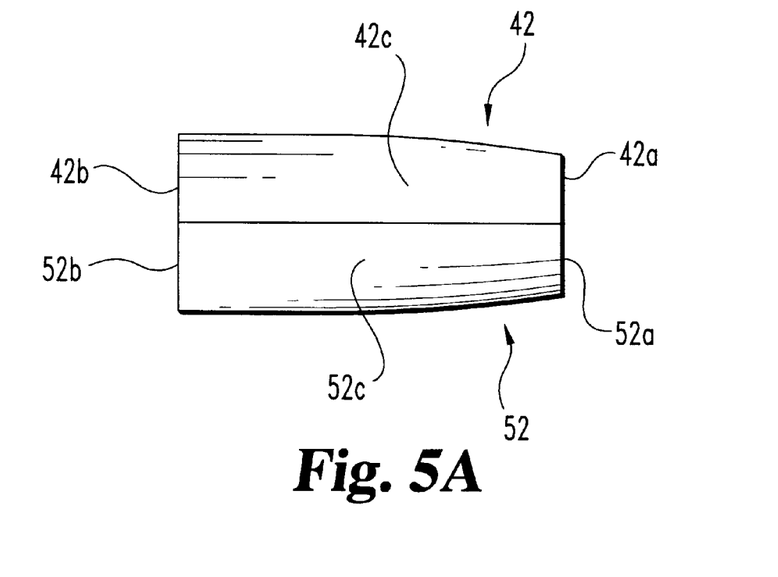
FIGS. 5A–5C are views of a first wedge and a second wedge of the surgical instrument of FIGS. 4A and 4B.
Figure 5B:
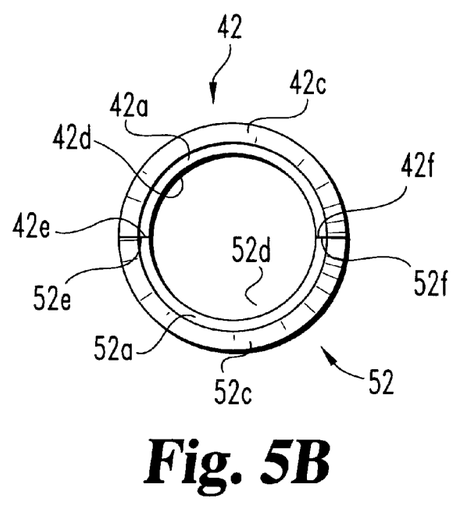
Figure 5C:
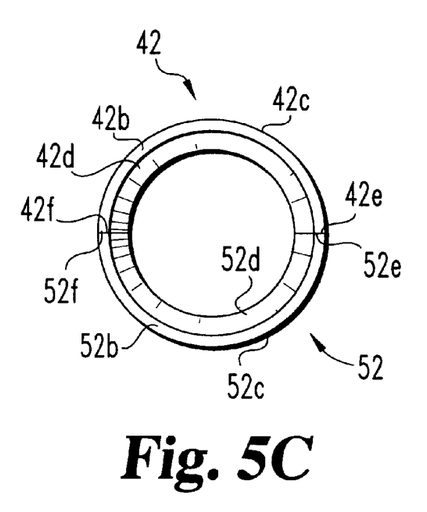

FIG. 5A is an enlarged side view of wedge 42 and wedge 52 in a closed position, FIG. 5B is an enlarged front view of wedge 42 and wedge 52 in a closed position, and FIG. 5C is an enlarged rear view of wedge 42 and wedge 52 in a closed position. Referring to FIGS. 5A–5C, wedge 42 has a blunted leading edge 42a, a rear edge 42b, a convex surface 42c tapering from rear edge 42b to blunted leading edge 42a, a concave surface 42d tapering from rear edge 42b to blunted leading edge 42a, a first side edge 42e and a second side edge 42f. Wedge 52 has a blunted leading edge 52a, a rear edge 52b, a convex surface 52c tapering from rear edge 52b to blunted leading edge 52a, a concave surface 52d tapering from rear edge 52b to blunted leading edge 52a, a first side edge 52e and a second side edge 52f. Concave surface 42d and concave surface 52d are proximally positioned to some extent when wedge 42 and wedge 52 are in a closed position. Preferably, first side edge 42e of wedge 42 and first side edge 52e of wedge 52 abut, and second side edge 42f of wedge 42 and second side edge 52f of wedge 52 abut when wedge 42 and wedge 52 are in a closed position as best shown in FIGS. 5B and 5C. Convex surface 42c of wedge 42 is integrated to distal end 41a of arm 41 (not shown in FIGS. 5A–5C), and convex surface 52c of wedge 52 is integrated to distal end 51a of arm 51 (not shown in FIGS. 5A–5C) as best shown in FIGS. 4A and 4B.

Referring back to FIGS. 5A–5C, blunted leading edge 42a of wedge 42 and blunted leading edge 52a of wedge 52 are sized and shaped to be lodged adjacent an adhesion interface of a patient's tissue and a permeable member of a catheter when wedge 42 and wedge 52 are in a closed position as further described in FIGS. 6A–6F, and accompanying text. It is to be appreciated and understood that the size and shape of a permeable member of a catheter can vary. Thus, the present invention contemplates that the size and shape of blunted leading edge 42a and blunted leading edge 52a can vary. For purposes of describing surgical instrument 30, blunted leading edge 42a and blunted leading edge 52a are shown in FIGS. 5B and 5C as having a semi-circular configuration whereby blunted leading edge 42a and blunted leading edge 52a can be lodged adjacent an adhesion interface of a patient's tissue and a substantially cylindrical permeable member of a catheter, e.g. cuff 12 of catheter 10 as shown in FIG. 1, when wedge 42 and wedge 52 are in a closed position.

Referring back to FIGS. 5A–5C, concave surface 42d of wedge 42 and concave surface 52d of wedge 52 are sized and shaped to clench a permeable member of a catheter when wedge 42 and wedge 52 are in a closed position as further described in FIGS. 6A–6F, and accompanying text. Again, it is to be appreciated and understood that the size and shape of a permeable member of a catheter can vary. Thus, the present invention contemplates that the size and shape of concave surface 42d and concave surface 52d can vary. For purposes of describing surgical instrument 30, concave surface 42d and concave surface 52d are shown as having a semi-cylindrical configuration in FIGS. 5B and 5C whereby concave surface 42d and concave surface 52d can clench a substantially cylindrical permeable member of a catheter, e.g. cuff 12 of catheter 10 as shown in FIG. 1, when wedge 42 and wedge 52 are in a closed position.

Figure 6A:
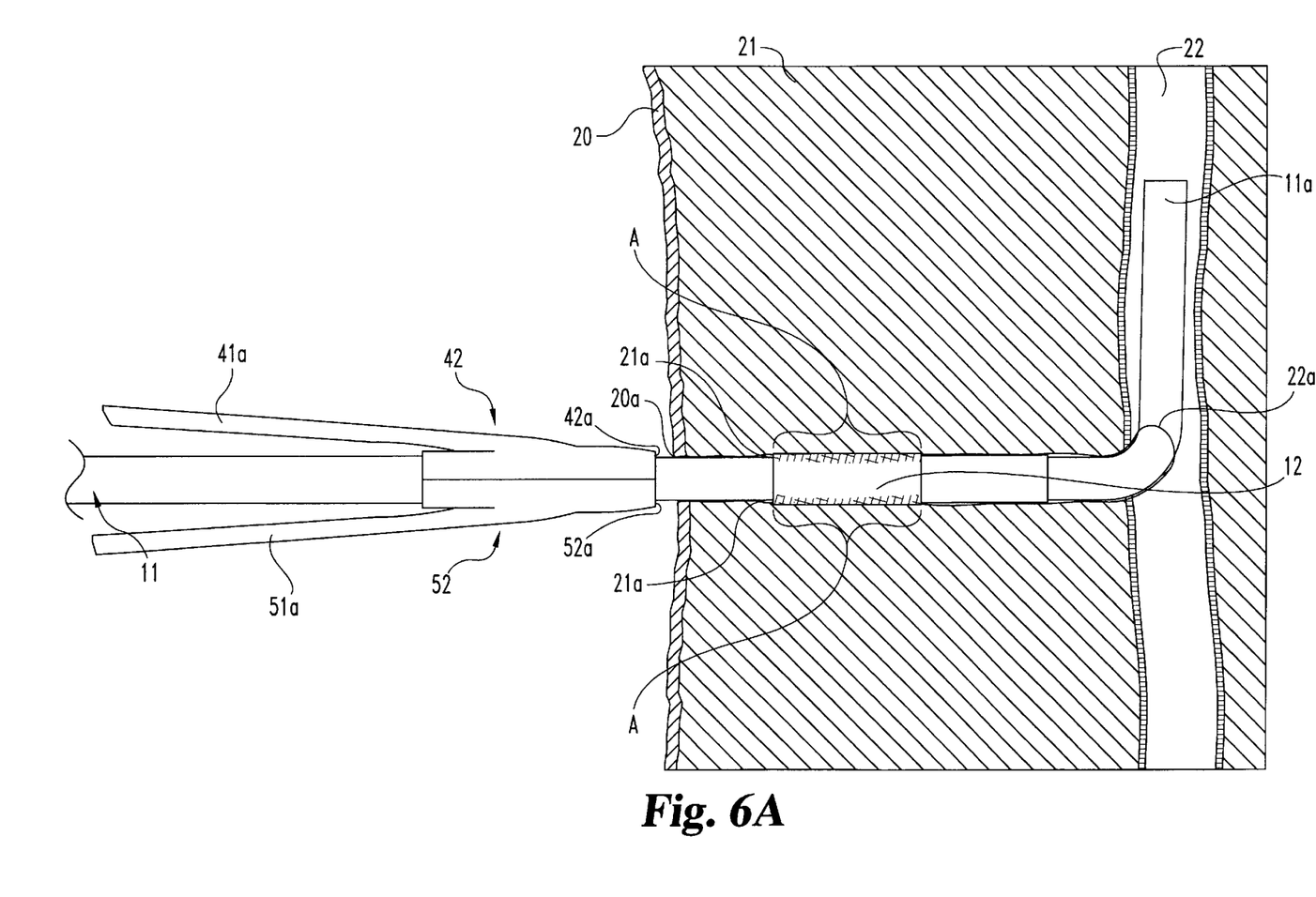
FIGS. 6A–6F are views of an exemplary illustration of an utilization of the surgical instrument of FIGS. 4A and 4B extracting tissue ingrowth from the cuff of the implanted catheter of FIG. 2.
Figure 6B:
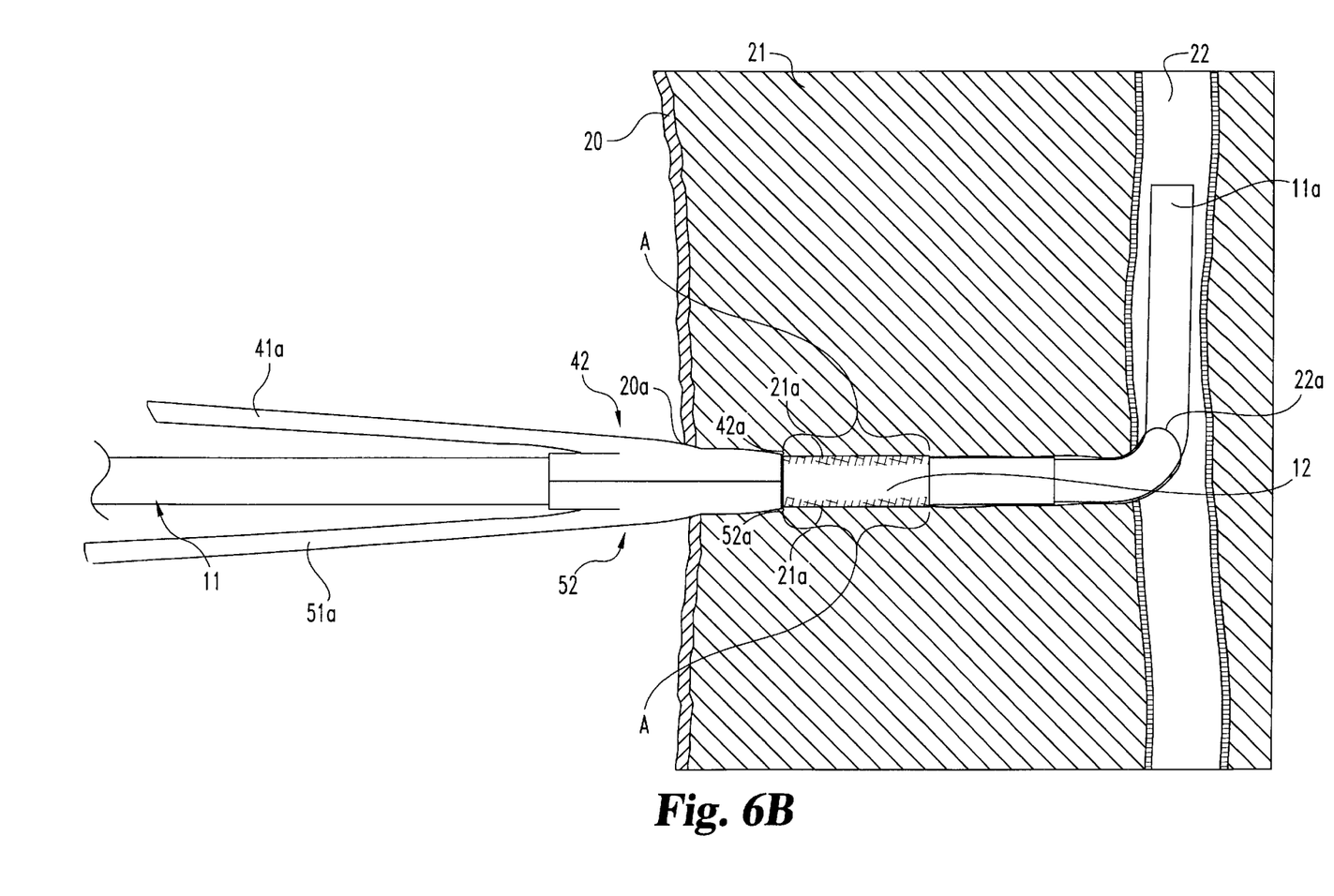

An exemplary illustration of an utilization of surgical instrument 30 to extract tissue ingrowth 21a from cuff 12 of an implanted catheter 10 as shown in FIG. 2 will now be described herein. Referring to FIG. 6A, wedge 42 and wedge 52 are pivotally moved to an open position via finger hole 43 (not shown) and finger hole 53 (not shown) to receive catheter tube 11, and then wedge 42 and wedge 52 are pivotally moved to a closed position to secure catheter tube 11 between wedge 42 and wedge 52. Referring to FIG. 3B, antecedently, concurrently or subsequently to securing catheter tube 11 between wedge 42 and wedge 52, skin entry point 20a is expanded as necessary to receive wedge 42 and wedge 52. The present invention contemplates that the expansion of skin entry point 20a may be partially or entirely achieved by closing and opening wedge 42 and wedge 52 as needed. Wedge 42 and wedge 52 are then inserted through skin entry point 20a, and advanced through subcutaneous tunnel 23 until blunted leading edge 42a and blunted leading edge 52a are lodged adjacent an adhesion interface A of cuff 12 and tissue 21. The present invention contemplates that wedge 42 and wedge 52 can be opened and closed as needed to facilitate the insertion and advancement of wedge 42 and wedge 52 through subcutaneous tunnel 23.

Figure 6C:
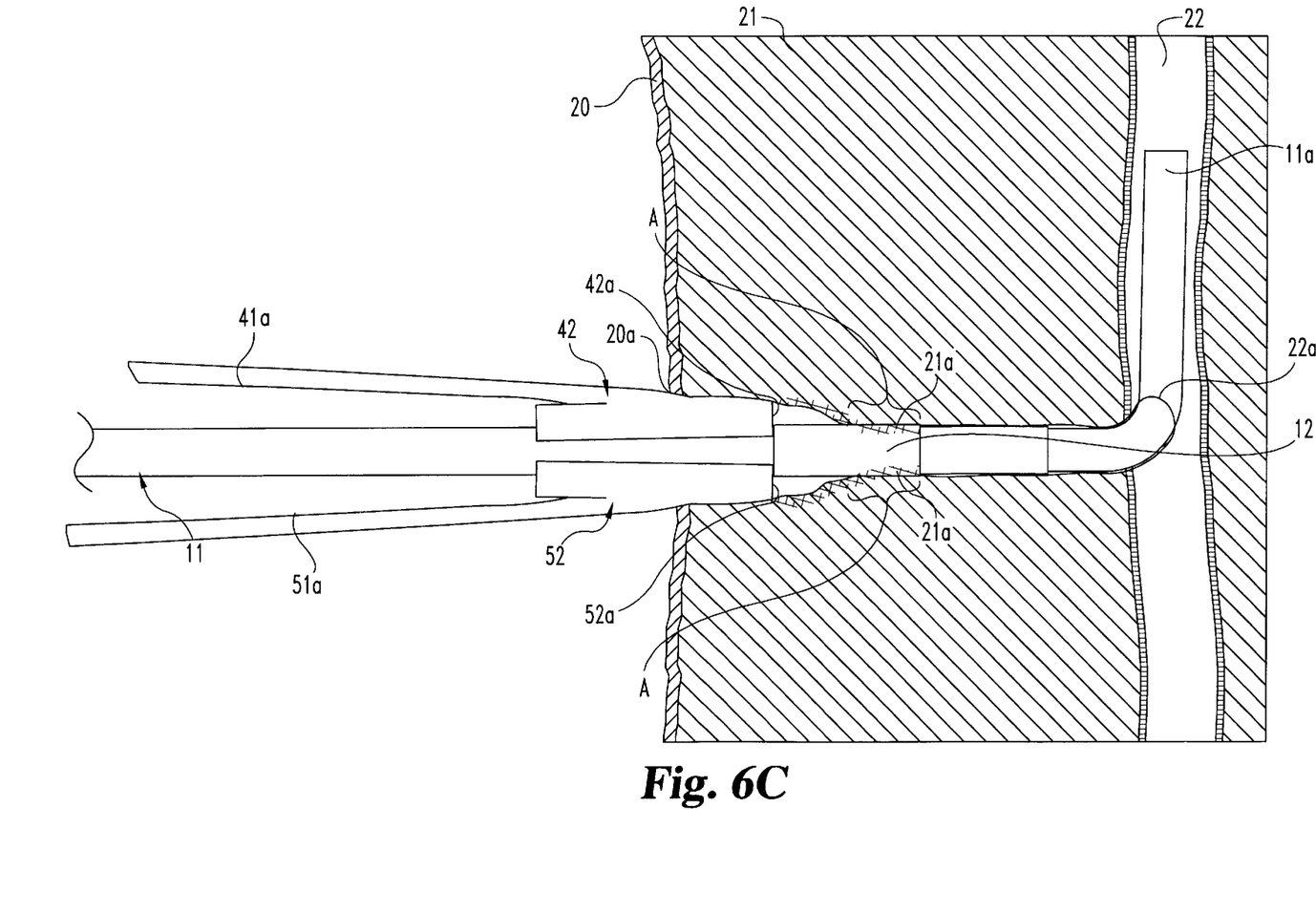
Figure 6D:
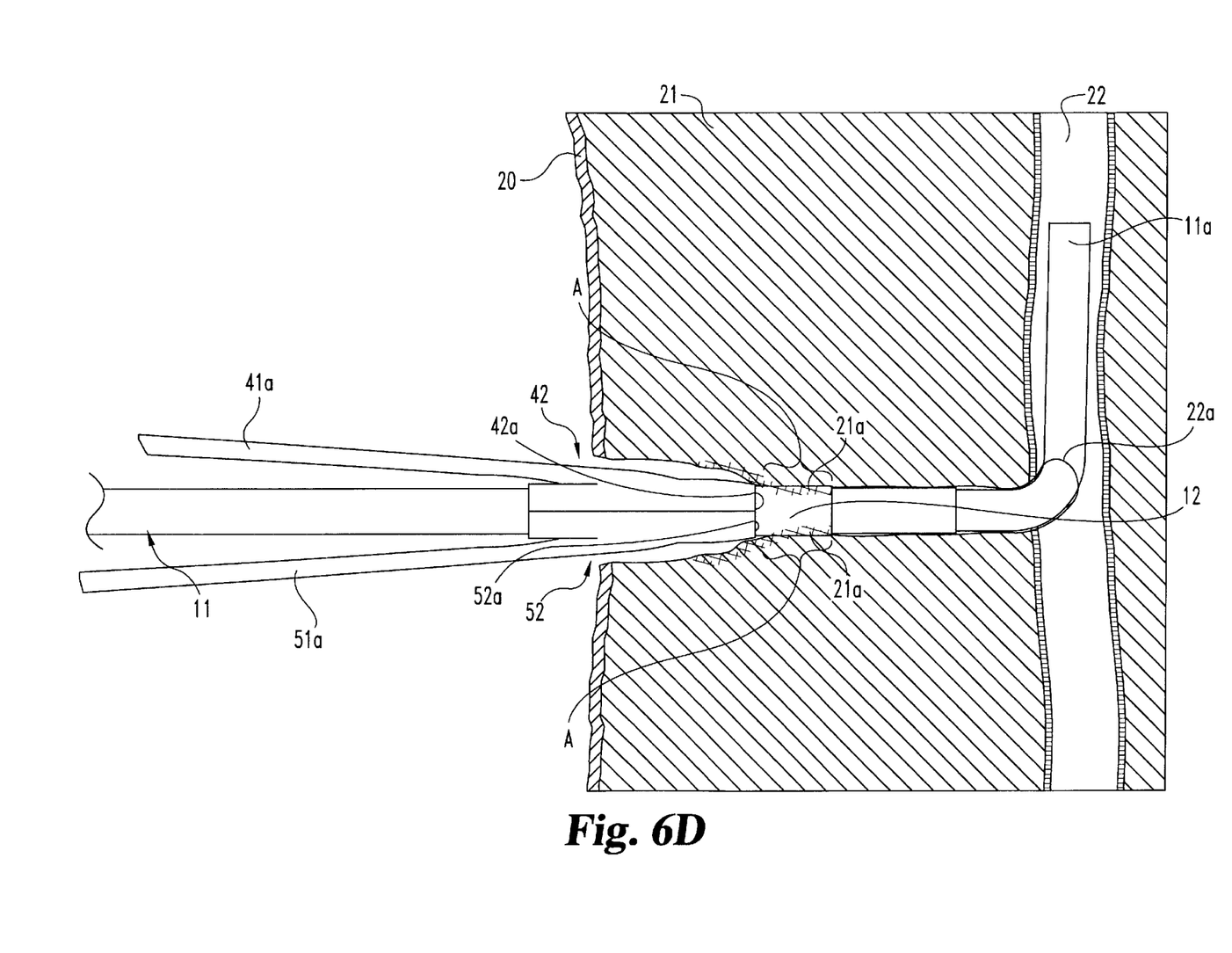
Figure 6E:
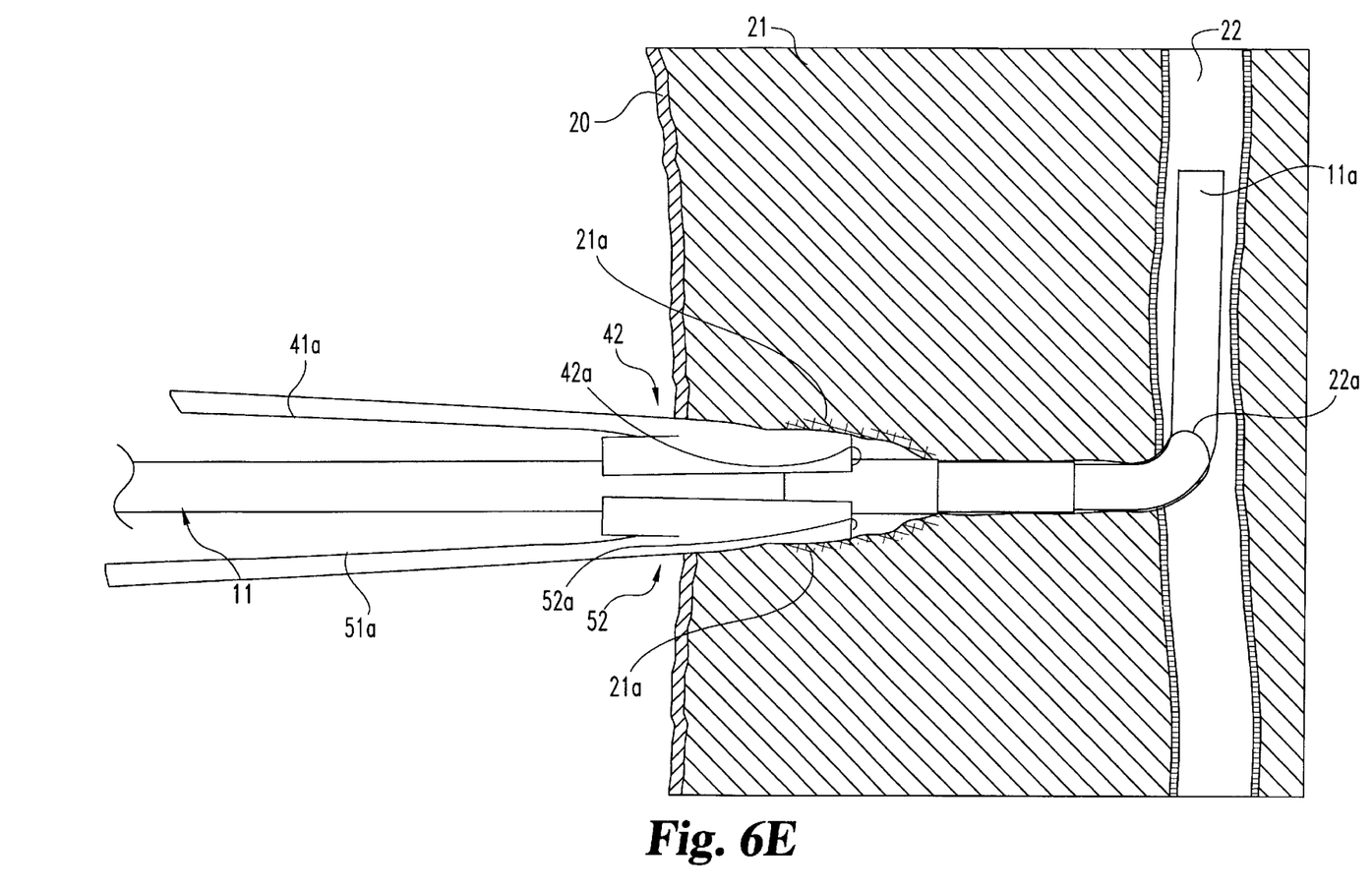
Figure 6F:
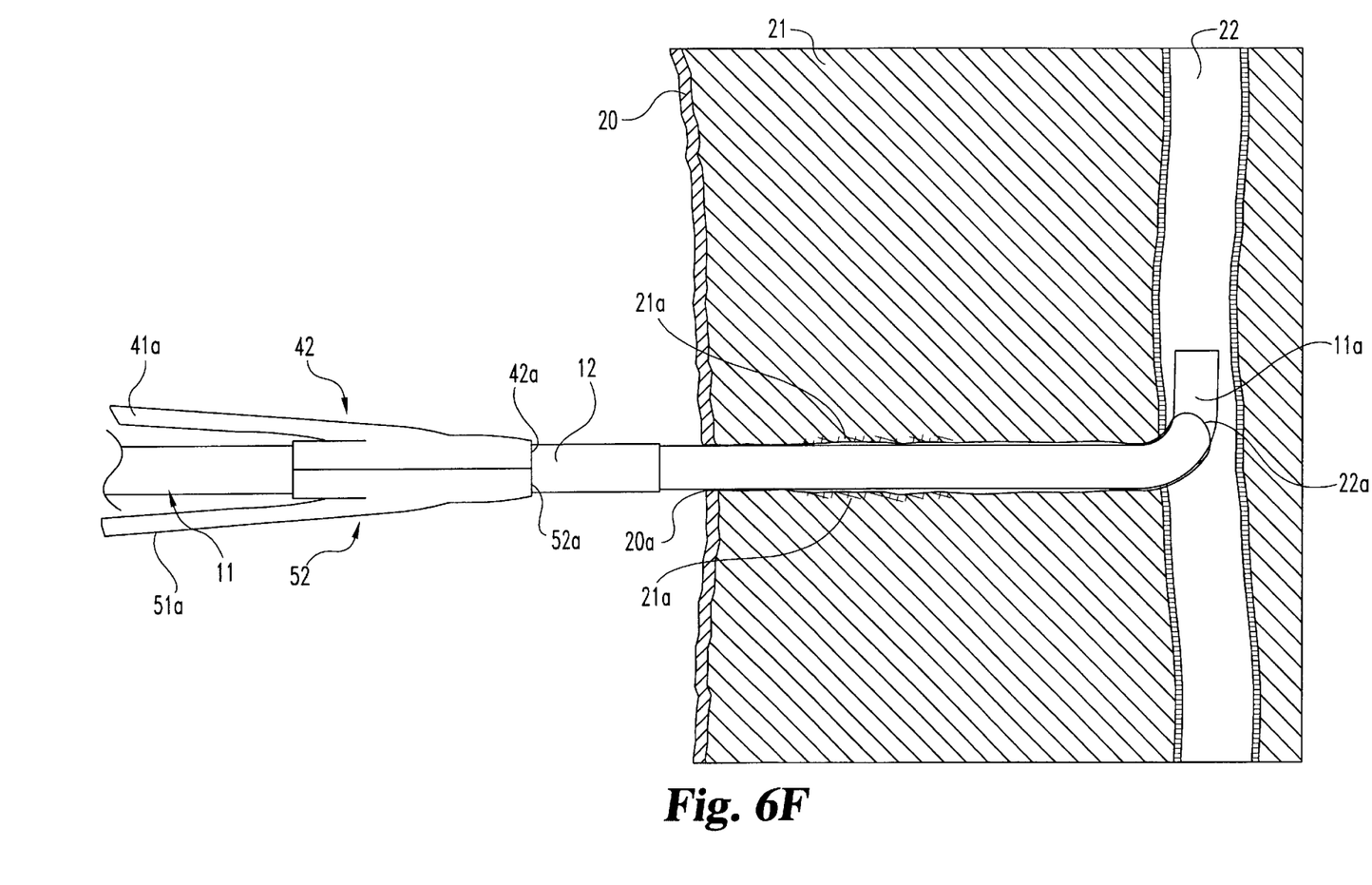

Referring to FIG. 6C, upon lodging blunted leading edge 42a and blunted leading edge 52a adjacent adhesion interface A, wedge 42 and wedge 52 are pivotally moved to an open position whereby portion 21a of tissue 21 is forcibly pulled out of cuff 12. It is to be appreciated and understood that depending on the length of cuff 12, all of portion 21a of tissue 21 may or may not be forcibly pulled out of cuff 12 when wedge 42 and wedge 52 are pivotally moved to an open position. For this exemplary illustration, half of portion 21a of tissue 21 is shown as being forcibly pulled out of cuff 12. Therefore, wedge 42 and wedge 52 are pivotally moved to a closed position and further advanced through subcutaneous tunnel 23 until blunted leading edge 42a and blunted leading edge 52a are relodged adjacent adhesion interface A of cuff 12 and tissue 21 as shown in FIG. 6D. Subsequently, wedge 42 and wedge 52 are again pivotally moved to an open position whereby the remaining half of portion 21a of tissue 21 is forcibly pulled out of cuff 12 as shown in FIG. 6E. Referring to FIG. 6F, upon the complete extraction of portion 21a of tissue 21 from cuff 12, wedge 42 and wedge 52 are pivotally moved to a closed position whereby concave surface 42d and concave surface 52d clench cuff 12 and cuff 12 can be removed from subcutaneous tunnel 23. It is to be appreciated and understood that the lodging of blunted leading edge 42 and blunted leading edge 52 and the forcible pulling of portion 21a of tissue 21 from cuff 12 by wedge 42 and wedge 52 should not dissect any portion of tissue 21. Consequently, it is to be further appreciated and understood that the likelihood of bleeding through subcutaneous channel 23 is significantly reduced.

Figures 7A, 7B, 7C:
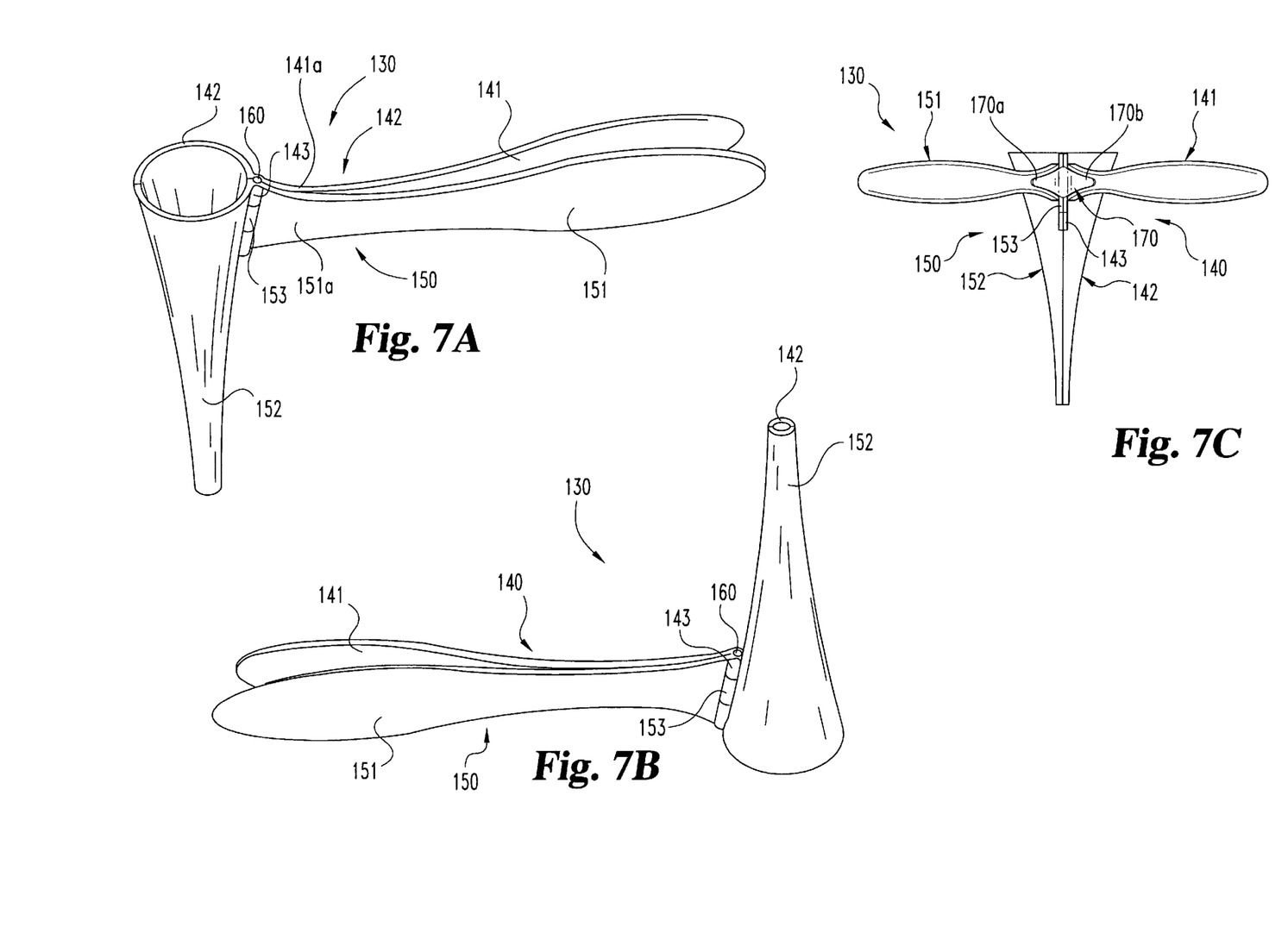
FIGS. 7A–7G are views of a second preferred embodiment of a surgical instrument for extracting tissue ingrowth from the cuff of the implanted catheter of FIG. 2.

FIG. 7A is a user end or perspective view of a surgical instrument 130 in accordance with a second preferred embodiment of the present invention, FIG. 7B is a working tip end or front perspective view of surgical instrument 130, and FIG. 7C is a between-handle view of surgical instrument 130. Referring to FIGS. 7A–7C, surgical instrument 130 comprises a first extracting component 140, a second extracting component 150, a pivot pin 160, and a spring 170. First extracting component 140 includes a handle 141, a wedge 142, and a hinge component 143 integrated to a top end 141a of handle 141 and to wedge 142. Second extracting component 150 includes a handle 151, a wedge 152, and a hinge component 153 integrated to a top end 151a of handle 151 and to wedge 152. Hinge component 143 and hinge component 153 are mated to constitute a hinge. Pivot pin 160 is inserted into hinge component 143 and hinge component 153 to thereby allow a user of surgical instrument 130 to pivotally move wedge 142 and wedge 152 to a closed position or to an open position via handle 141 and handle 151. A closed position of wedge 142 and wedge 152 occurs when wedge 142 and wedge 152 are proximally positioned to some extent. Preferably, wedge 142 and wedge 152 abut when in a closed position, for example, as shown in FIGS. 7A–7E. Wedge 142 and wedge 152 constitute a radially expandable wedge assembly when in a closed position. An open position of wedge 142 and wedge 152 occurs when wedge 142 and wedge 152 are spaced apart to some extent, for example, as shown in FIGS. 7F and 7G, and described in accompanying text. Spring 170 has a first end 170a affixed to handle 151 of extracting component 150, and a second end 170b affixed to handle 141 of extracting component 140 to thereby bias wedge 142 and wedge 152 into a closed position.

Figure 7D:
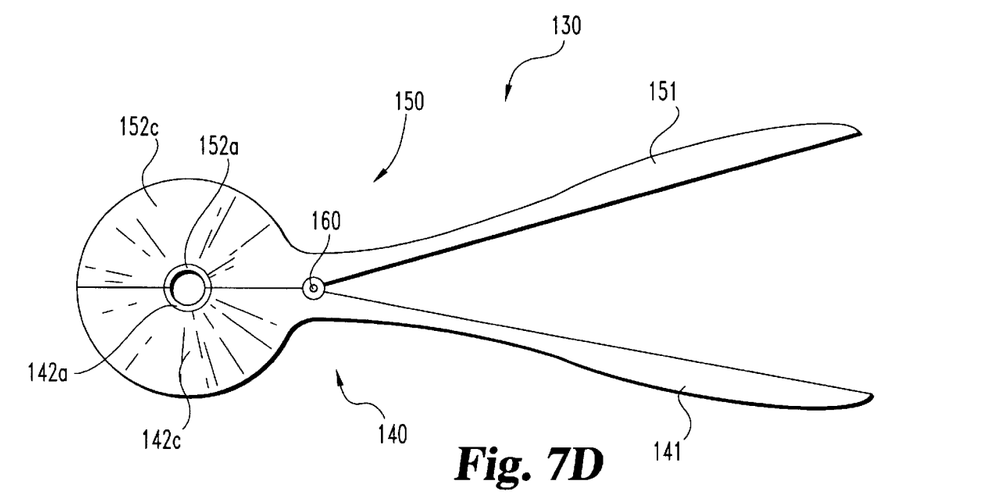
Figure 7E:
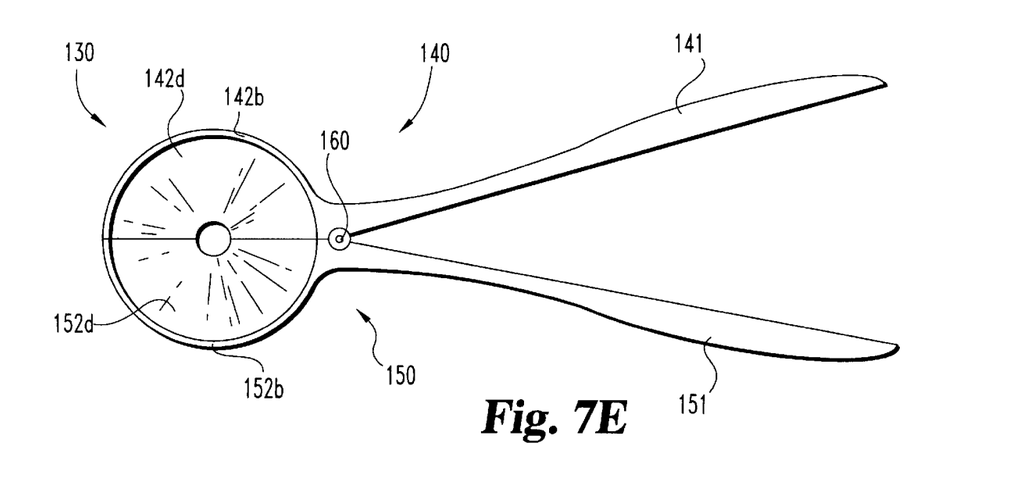
Figure 7F:
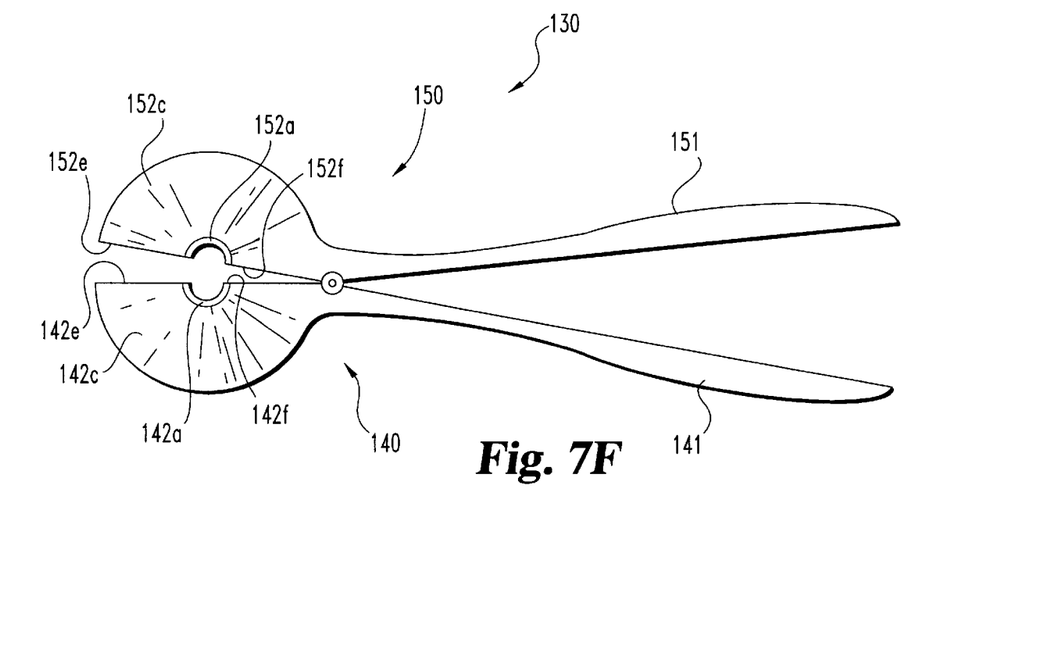
Figure 7G:
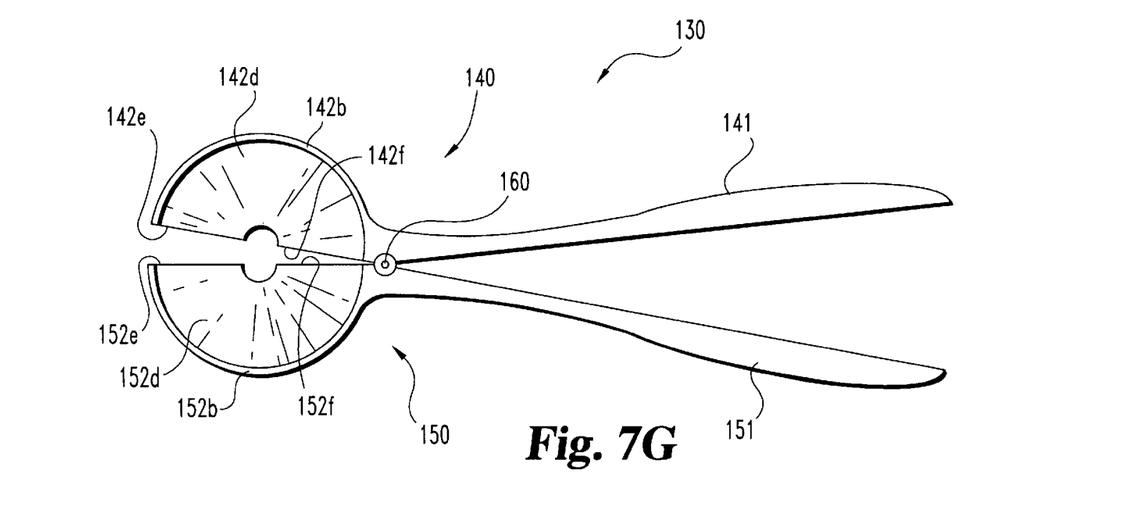

FIG. 7D is a front view of wedge 142 and wedge 152 in a closed position, and FIG. 7E is a rear view of wedge 142 and wedge 152 in a closed position. FIG. 7F is front view of wedge 142 and wedge 152 in an open position, and FIG. 7G is a rear view of wedge 142 and wedge 152 in an open position. Referring to FIGS. 7D–7G, wedge 142 has a blunted leading edge 142a, a rear edge 142b, a convex surface 142c tapering from rear edge 142b to blunted leading edge 142a, a concave surface 142d tapering from rear edge 142b to blunted leading edge 142a, a first side edge 142e and a second side edge 142f. Wedge 152 has a blunted leading edge 152a, a rear edge 152b, a convex surface 152c tapering from rear edge 152b to blunted leading edge 152a, a concave surface 152d tapering from rear edge 152b to blunted leading edge 152a, a first side edge 152e and a second side edge 152f. Preferably, side edge 142e of wedge 142 and side edge 152e of wedge 152 abut, and side edge 142f of wedge 142 and side edge 152f of wedge 152 abut when wedge 142 wedge 152 are in a closed position as shown in FIGS. 7D and 7E. Side edge 142e of wedge 142 and side edge 152e of wedge 152 are spaced apart, and side edge 142f of wedge 142 and side edge 152f of wedge 152 are spaced apart when wedge 142 wedge 152 are in an open position as shown in FIGS. 7F and 7G.

As with blunted leading edge 42a of wedge 42 and blunted leading edge 52a of wedge 52, blunted leading edge 142a of wedge 142 and blunted leading edge 152a of wedge 152 are sized and shaped to be lodged adjacent an adhesion interface of a patient's tissue and a permeable member of a catheter when wedge 142 and wedge 152 are in a closed position. It is to be appreciated and understood that the size and shape of a permeable member of a catheter can vary. Thus, the present invention contemplates that the size and shape of blunted leading edge 142a and blunted leading edge 152a can vary. For purposes of describing surgical instrument 130, blunted leading edge 142a and blunted leading edge 152a are shown in FIGS. 7D–7G as having semi-circular configurations whereby blunted leading edge 142a and blunted leading edge 152a can be lodged adjacent an adhesion interface of a patient's tissue and a substantially cylindrical permeable member of a catheter, e.g. cuff 12 of catheter 10 as shown in FIG. 1, when wedge 142 and wedge 152 are in a closed position.

Referring back to FIGS. 7D–7G, as with concave surface 42d of wedge 42 and concave surface 52d of wedge 52, concave surface 142d of wedge 142 and concave surface 152d of wedge 152 are sized and shaped to clench a permeable member of a catheter when wedge 142 and wedge 152 are in a closed position. Again, it is to be appreciated and understood that the size and shape of a permeable member of a catheter can vary. Thus, the present invention contemplates that the size and shape of concave surface 142d and concave surface 152d can vary. For purposes of describing surgical instrument 130, concave surface 142d and concave surface 152d are shown in FIGS. 7D–7G as having semi-cylindrical configuration whereby concave surface 142d and concave surface 152d can clench a substantially cylindrical permeable member of a catheter, e.g. cuff 12 of catheter 10 as shown in FIG. 1, when wedge 142 and wedge 152 are in a closed position.

While the present invention has been illustrated and described in detail in the drawings and foregoing description, the same is to be considered as illustrative and not restrictive in character, it being understood that the preferred embodiments have been shown and described and that all changes and modifications that come within the spirit of the invention are desired to be protected.

What is claimed is:

1. A method for extracting a catheter from an animal body site in which there has been tissue ingrowth in a permeable member affixed around the catheter, said method comprising the steps of:
   (a) mounting a radially expandable wedge assembly on the catheter;
   (b) inserting a working end of the wedge assembly into the tissue at the body site; and
   (c) spreading the working end of the wedge assembly radially with respect to the catheter at the site to thereby pull the tissue ingrowth out of the permeable member.

2. The method of claim 1 further comprising a step (d) of clenching the catheter with the working end of the wedge assembly following a complete extraction of the tissue ingrowth from the permeable member and then pulling the catheter out of the body site.

3. A method for extracting a tissue ingrowth out of a permeable member affixed around a catheter tube, the catheter tube having a first portion outside of the patient and a second portion inserted through a subcutaneous tunnel of a patient, the permeable member being disposed within the subcutaneous tunnel of the patient, the permeable member having an adhesion interface with a tissue of the patient, said method utilizing a surgical instrument comprising a first extracting component including a first wedge and a second extracting component including a second wedge, the first extracting component and the second extracting component pivotally coupled to move the first wedge and the second wedge to an open position or a closed position, said method comprising the steps of:
   (a) mounting the first wedge and the second wedge on the first portion of the catheter tube;
   (b) inserting the first wedge and the second wedge into the subcutaneous tunnel;

(c) advancing the first wedge and the second wedge along the second portion of the catheter tube;

(d) pivotally moving the first wedge and the second wedge to the closed position as the first wedge and the second wedge are advanced along the second portion of the catheter tube to lodge the first wedge and the second wedge adjacent the adhesion interface of the permeable member and the tissue of the patient; and (e) subsequently pivotally moving the lodged first wedge and second wedge to the open position to forcibly pull the tissue ingrowth out of the permeable member.

4. The method of claim 3 wherein said step (a) includes pivotally moving the first wedge and the second wedge to the open position to receive the first portion of the catheter tube therebetween, and pivotally moving the first wedge and the second wedge to the closed position to secure the first portion of the catheter tube therebetween.

5. The method of claim 3 wherein said step (b) includes pivotally moving the first wedge and the second wedge to the open position and/or the closed position as needed to facilitate said insertion of the first wedge and the second wedge into the subcutaneous tunnel of the patient.

6. The method of claim 3 wherein said step (c) includes pivotally moving the first wedge and the second wedge to the open position and/or the closed position as needed to facilitate said advancement of the first wedge and the second wedge along the second portion of the catheter tube.

7. The method of claim 3 further comprising a step (f) of repeating steps (c), and (e) as required to completely extract the tissue ingrowth out of the permeable member.

8. The method of claim 7 further comprising a step (g) of pivotally moving the first wedge and the second wedge to a closed position upon a complete extraction of the tissue ingrowth from the permeable member to clench the permeable member whereby the second portion of the catheter tube can be removed from the subcutaneous tunnel of the patient.

* * * * *